United States Patent [19]

Morabito et al.

[11] Patent Number: 5,338,514
[45] Date of Patent: Aug. 16, 1994

[54] VENTED CAPILLARY GAS CHROMATOGRAPHY APPARATUS

[75] Inventors: Paul L. Morabito; Terrence McCabe; Joseph F. Hiller, all of Midland, Mich.

[73] Assignee: The Dow Chemical Company, Midland, Mich.

[21] Appl. No.: 111,808

[22] Filed: Aug. 25, 1993

[51] Int. Cl.$^5$ .................................... G01N 30/00
[52] U.S. Cl. ................... 422/89; 73/23.42; 96/105; 436/161
[58] Field of Search .............. 422/89; 436/161; 95/85, 95/89; 96/105, 107; 137/625.19, 625.46; 73/23.35, 23.37, 23.41, 23.42

[56] References Cited

U.S. PATENT DOCUMENTS

| | | | |
|---|---|---|---|
| 3,518,059 | 6/1970 | Levy | 73/23.41 |
| 4,066,402 | 1/1978 | Komiyama et al. | 422/89 |
| 4,077,773 | 3/1978 | Stearns | 422/89 |
| 4,305,906 | 12/1981 | Mikasa et al. | 422/89 |
| 4,500,432 | 2/1985 | Poole et al. | 96/105 |
| 4,553,985 | 11/1985 | Dahlgren et al. | 73/23.42 |
| 4,588,422 | 5/1986 | Raimond | 73/23.55 |
| 5,034,193 | 7/1991 | Maroulis et al. | 422/89 |
| 5,049,509 | 9/1991 | Szakasits et al. | 422/89 |
| 5,152,176 | 10/1992 | Bryselbont et al. | 422/89 |

Primary Examiner—James C. Housel
Assistant Examiner—Laura E. Collins
Attorney, Agent, or Firm—Timothy S. Stevens

[57] ABSTRACT

Method and apparatus for gas chromatography/mass spectroscopy including a retention gap, a capillary gas chromatography column and a mass spectrometer, the improvement being a valve that facilitates temporarily venting the carrier gas from between the retention gap and the capillary gas chromatography column immediately after the injection of a sample. The valve also facilitates an alternate flow of carrier gas into the mass spectrometer during the venting operation.

4 Claims, 3 Drawing Sheets

VENTED CAPILLARY GAS CHROMATOGRAPHY APPARATUS

BACKGROUND OF THE INVENTION

Capillary gas chromatography is one of the most important and well-developed methods of chemical analysis. Vented capillary gas chromatography is known and is used for large volume sample injections to minimize interference from the relatively large volume of sample solvent inherent in a large injection. The interference from the relatively large volume of solvent used is removed by venting carrier gas flow from the retention gap to waste for a limited time, long enough to discard much of the solvent without serious loss of sample components of interest.

Despite the usefulness of known vented capillary gas chromatographs, the art of vented capillary gas chromatography would be advanced if current technology could be better adapted for use with detectors like mass spectrometers which subject the outlet end of the capillary column to a partial vacuum.

SUMMARY OF THE INVENTION

The instant invention is a method and apparatus for vented capillary gas chromatography that is especially suitable for large volume on-column injection with detectors like mass spectrometers which subject the outlet end of the column to a partial vacuum. When the outlet end of a vented capillary gas chromatography column is subjected to a partial vacuum, then components of interest that have an atmospheric pressure boiling point of only 25 or 50 degrees centigrade higher than the solvent of the sample can be lost. Although not the only benefit, the primary benefit of the instant invention is the solution to this problem. Another important benefit of the instant invention is reduced shock to the detector because a gas is flowed to the detector to maintain a relatively constant pressure within the detector during the venting operation.

The instant invention is an improved vented capillary gas chromatograph of the type that generally includes a means for supplying a carrier gas, a means for injecting a liquid sample, a retention gap, a connector, a capillary gas chromatography column, and a detector each respectively in series fluid communication, a divert valve, the divert valve being in fluid communication with the connector, a vent restrictor and a bleed restrictor, the vent restrictor and the bleed restrictor each being in fluid communication with the divert valve so that the divert valve can alternatively provide fluid communication between the connector and the vent restrictor or between the connector and the bleed restrictor, the column having an inlet end and an outlet end, the inlet end of the column being connected to the connector. The improvement of this embodiment of the instant invention is to replace the divert valve with a multi-position fluid flow switch having at least two positions. The flow switch must be in fluid communication with a means for supplying a gas, with the connector, with the bleed restrictor, with the vent restrictor, with the outlet end of the column, and with the detector so that when the flow switch is in a first position, also referred to as the analysis position, the outlet end of the column is in fluid communication with the detector and the connector is in fluid communication with the bleed restrictor. Preferably, the means for supplying a gas is in fluid communication with the vent restrictor. On the other hand, when the flow switch is in a second position, also referred to as the vent position, the means for supplying a gas is in fluid communication with the detector, the outlet end of the column is in fluid communication with the bleed restrictor and the connector is in fluid communication with the vent restrictor.

The instant invention is also an improved vented capillary gas chromatograph of the type that generally includes a means for supplying a carrier gas, a means for injecting a liquid sample, a retention gap, a connector, a capillary gas chromatography column, and a detector each respectively in series fluid communication, a divert valve, the divert valve being in fluid communication with the connector, a vent restrictor, a bleed restrictor, the vent restrictor and the bleed restrictor each being in fluid communication with the divert valve so that the divert valve can alternatively provide fluid communication between the connector and the vent restrictor or between the connector and the bleed restrictor, the column having an inlet end and an outlet end, the inlet end of the column being connected to the connector. The improvement of this embodiment of the instant invention is a multi-position fluid flow switch having at least two positions, a flow restrictor and a column restrictor, the flow switch being in fluid communication with a source of gas, with the detector, with the outlet end of the column, with the column restrictor and with the flow restrictor so when the flow switch is in a first position, also referred to as the analysis position, the outlet end of the column is in fluid communication with the detector, and when the flow switch is in a second position, also referred to as the vent position, the outlet end of the column is in fluid communication with the column restrictor while the detector is in fluid communication with the source of gas. Preferably, when the flow switch is in its first or analysis position, the source of gas is in fluid communication with the flow restrictor.

The instant invention is also a method for vented capillary gas chromatography that necessarily includes six steps. The first step is to flow a stream of carrier gas through a retention gap. The second step is to inject a liquid sample into the retention gap, the liquid sample comprising a volatile solvent and a less volatile component of interest. The third step is to selectively vaporize the injected sample into the stream of carrier gas flowing through the retention gap so vaporized sample emerges from the retention gap in the stream of carrier gas flowing through the retention gap initially enriched with the volatile solvent of the injected sample and eventually enriched with the less volatile component of interest of the injected sample. The fourth step is to flow at least a portion of the stream of carrier gas emerging from the retention gap enriched with the volatile solvent of the injected sample to waste. The fifth step, which must be performed during the fourth step, is to flow a stream of proxy gas to a detector. The sixth step is to flow at least a portion of the stream of carrier gas emerging from the retention gap enriched with the component of interest of the injected sample through a capillary gas chromatography column to the detector.

BRIEF DESCRIPTION OF THE DRAWINGS

FIG. 2 shows the injection valve in the load position and the flow switching valve in the analysis position.

FIG. 4 shows the injection valve in the load position and the flow switching valve in the analysis position.

DETAILED DESCRIPTION OF THE INVENTION

Figure 1:
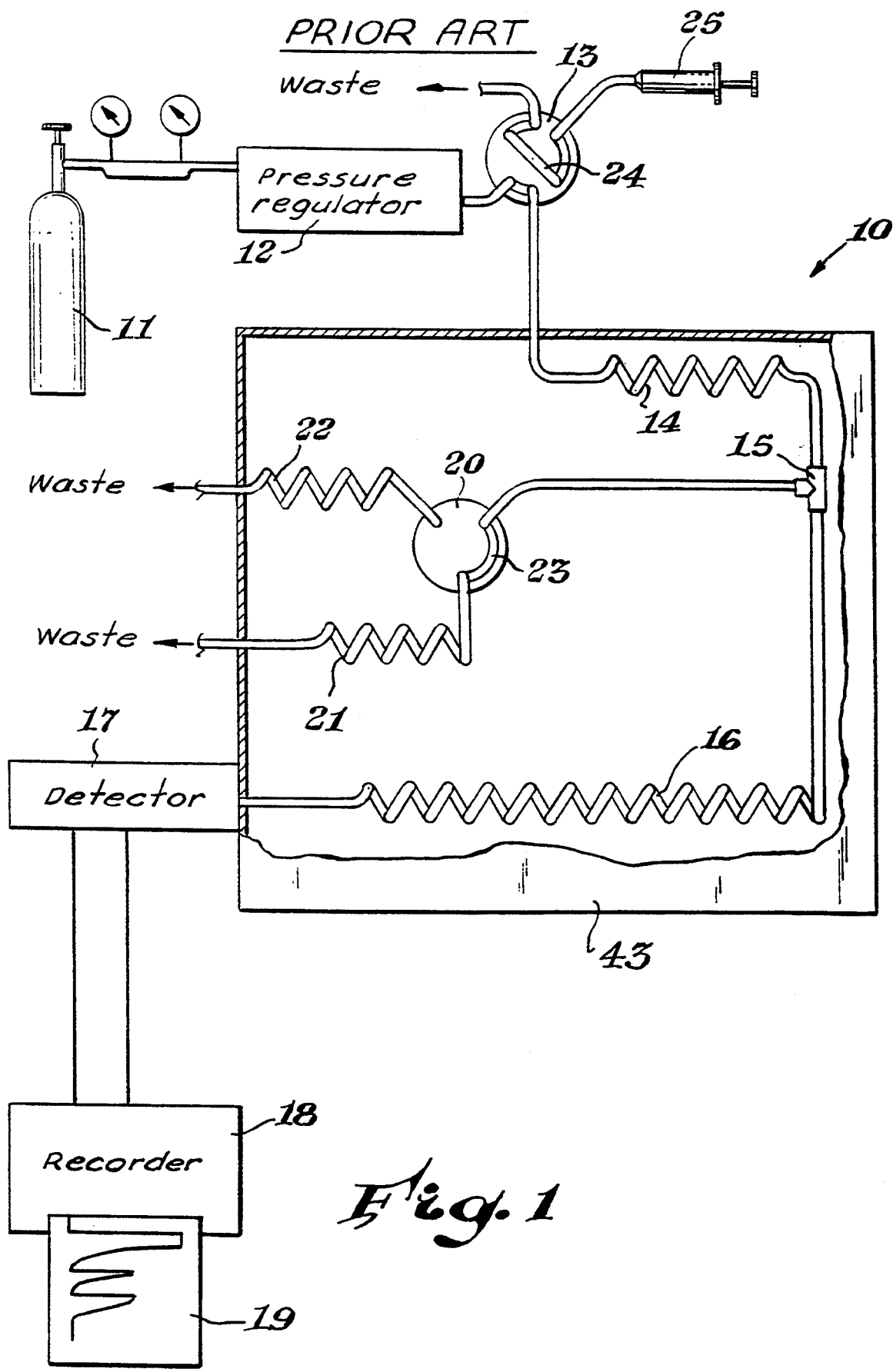
FIG. 1 is a part schematic and part full drawing of a prior art vented capillary gas chromatograph that includes a divert valve.

Referring now to FIG. 1, therein is shown a prior art vented capillary gas chromatograph 10 like the gas chromatograph of U.S. Pat. No. 5,048,322. The vented capillary gas chromatograph 10 includes a means for supplying a carrier gas, such as a cylinder of compressed carrier gas 11. The cylinder of compressed carrier gas 11 is connected by tubing to a carrier gas pressure regulator 12 which is connected by tubing to a means for injecting a liquid sample, such as a sample injection valve 13. The sample injection valve 13 is connected to a retention gap 14 which is connected to a connector, such as a tee 15. The tee 15 is connected to the inlet end of a capillary gas chromatography column 16. The outlet end of the capillary gas chromatography column 16 is connected to a detector 17. The detector is electrically connected by wires to a strip chart recorder 18 which is shown as having drawn a chromatogram 19.

The tee 15 in FIG. 1 is also connected by tubing to a divert valve 20 which is a means for directing gas flow to restrictors of different restricting capability. In addition to the tee 15, the divert valve 20 is connected to a bleed restrictor 21 and a vent restrictor 22 which may be lengths of capillary tubing. The divert valve 20 has an internal passageway 23 shown as providing fluid communication between the tee 15 and the bleed restrictor 21. The internal passageway 23 of the divert valve 20 can be rotated so fluid communication is instead provided between the tee 15 and the vent restrictor 22. The injection valve 13 is provided with an injection loop 24 such as a length of capillary tubing having a relatively large volume. A syringe 25 is connected to the injection valve 13 and the syringe 25 is used to fill the loop 24 with a liquid sample.

The retention gap 14, the tee 15, the column 16, the valve 20, the bleed restrictor 21 and the vent restrictor 22 are all contained in an oven 43.

The teachings of U.S. Pat. Nos. 5,001,071 and 5,048,322 are hereby incorporated by reference to provide the reader hereof with a more complete understanding of the construction and operation of the prior art vented capillary gas chromatograph shown in FIG. 1.

Figure 2:
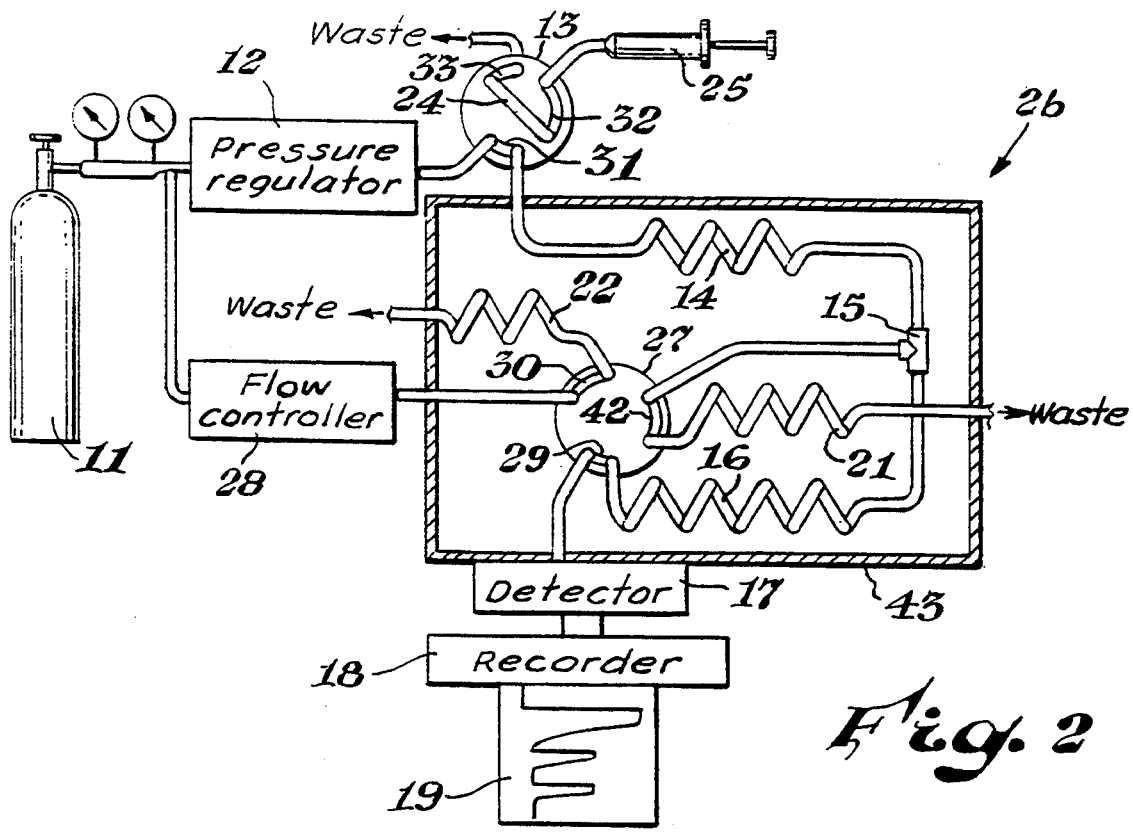
FIG. 2 is a part schematic and part full drawing of a vented capillary gas chromatograph of the instant invention which is similar to FIG. 1 except that the divert valve of FIG. 1 is now replaced with a flow switching valve and a carrier gas flow controller is added.
Figure 3:
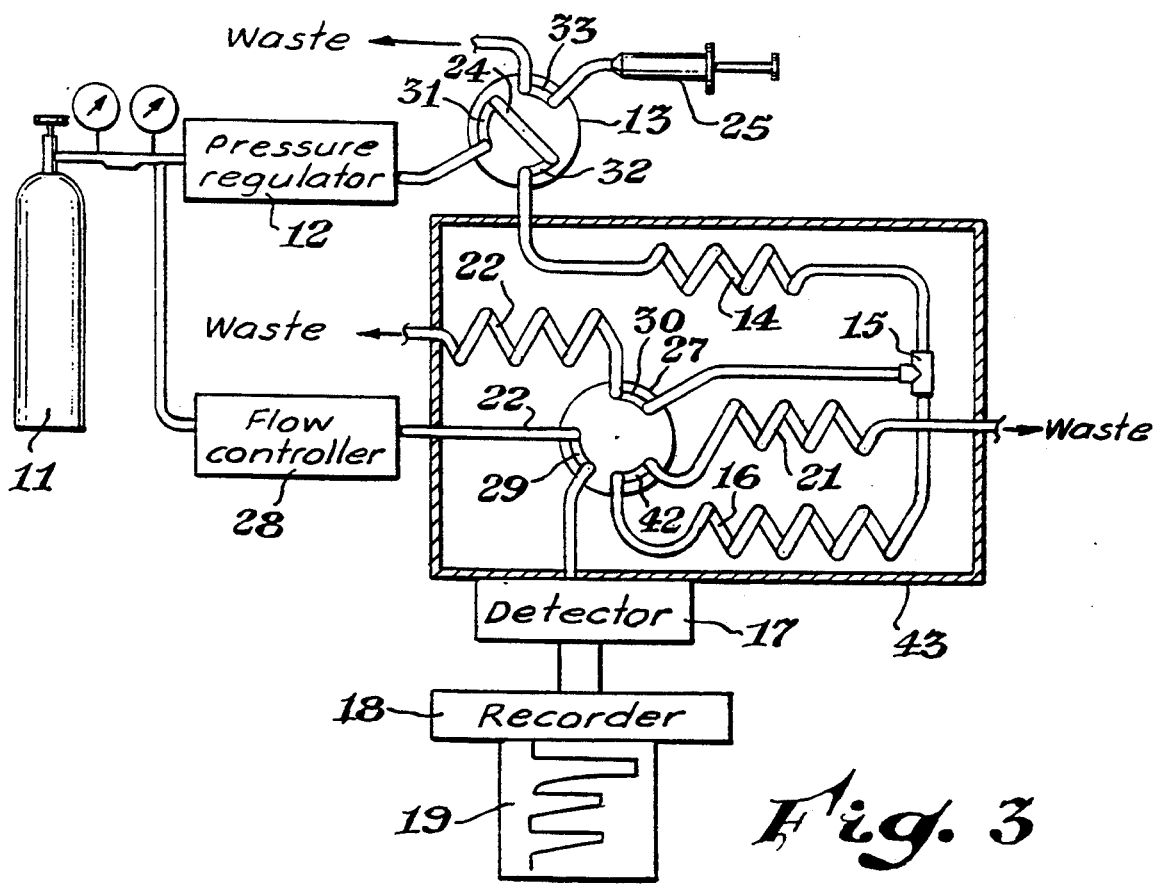
FIG. 3 shows the same apparatus as FIG. 2 but shows the injection valve in the inject position and shows the flow switching valve in the vent position wherein, during the venting step, carrier gas is flowed from the added carrier gas flow controller through the flow switching valve to the detector.

The instant invention, in its apparatus embodiments, is an improvement on the type of vented capillary gas chromatograph shown in FIG. 1. Referring now to FIGS. 2 and 3, therein is shown a vented capillary gas chromatograph 26 in one embodiment of the instant invention. A comparison between FIG. 1 and FIGS. 2 and 3 will reveal many similarities. Therefore, the elements of FIGS. 2 and 3 that are the same as the elements of FIG. 1 are given the same reference numerals. However, a comparison between FIG. 1 and FIGS. 2 and 3 will also reveal that the divert valve 20 of FIG. 1 has been replaced with a multi-position fluid flow switch having at least two positions, i.e., the flow switching valve 27. In addition, a carrier gas flow controller 28 is connected by tubing to the cylinder 11 and to the switching valve 27 in order to supply gas to the switching valve 27.

The retention gap 14, the tee 15, the column 16, the flow switching valve 27, the bleed restrictor 21 and the vent restrictor 22 are all contained in an oven 43.

As shown in FIG. 2, the switching valve 27 is in its first or analysis position. The switching valve 27 contains a first passageway 42, a second passageway 29 and a third passageway 30. When the switching valve 27 is in the position shown in FIG. 2, the outlet end of the column 16 is in fluid communication with the detector 17 via the passageway 29, and the tee 15 is in fluid communication with the bleed restrictor 21 via the passageway 42. Preferably, when the switching valve 27 is in its first or analysis position, the carrier gas flow controller 28 is in fluid communication with the vent restrictor 22 via the passageway 30. Alternatively, the gas from the flow controller 28 need not flow through a vent restrictor 22 to waste when the valve 27 is in its analysis position. For example, the connection between the flow controller 28 and the switching valve 27 could be closed by a separate valve.

Also, as shown in FIG. 2, the injection valve 13 is in its load position such that the pressure regulator 12 is in fluid communication with the retention gap 14 via the passageway 31, the syringe 25 is in fluid communication with the injection loop 24 via the passageway 32, and the injection loop 24 in turn goes to waste via the passageway 33.

Referring now to FIG. 3, therein is shown the same apparatus as in FIG. 2 but with the switching valve 27 in a second or vent position and with the injection valve 13 in its inject position. When the switching valve 27 is in the position shown in FIG. 3, the second carrier gas flow controller 28 is in fluid communication with the detector 17 via the passageway 29, the outlet end of the column 16 is in fluid communication with the bleed restrictor 21 via the passageway 42, and the tee 15 is in fluid communication with the vent restrictor 22 via the passageway 30.

When the injection valve 13 is in its inject position, as shown in FIG. 3, the pressure regulator 12 is in fluid communication with the retention gap 14 via the passageway 31, the injection loop 24, and the passageway 32; and the syringe 25 is connected to waste via the passageway 33.

It should be understood that the flow controller 28 is but one of the many means for supplying a gas that could have been used. For example, the flow controller 28 could have been replaced with a simple valve. The means for supplying a gas need not necessarily supply the same gas as is used as the carrier gas. However, the use of the second flow controller 28 supplying the same gas as the carrier gas is highly preferred in the instant invention because the detector 17 then is exposed to the same gas whether the switching valve 27 is in its first position or its second position.

It should also be understood that the switching valve 27 is but one of the many multi-position fluid flow switches that could have been used. For example, a plurality of three way valves could have been used instead of the valve 27. However, the use of the valve 27 is highly preferred in the instant invention because it incorporates the needed function of the multi-position fluid flow switch into a single valve. It should also be possible to combine the function of the injection valve 13 with the function of the switching valve 27 into a single switching and injection valve; and such a combined valve is intended to be covered by the broad scope of the claims hereof.

Figure 4:
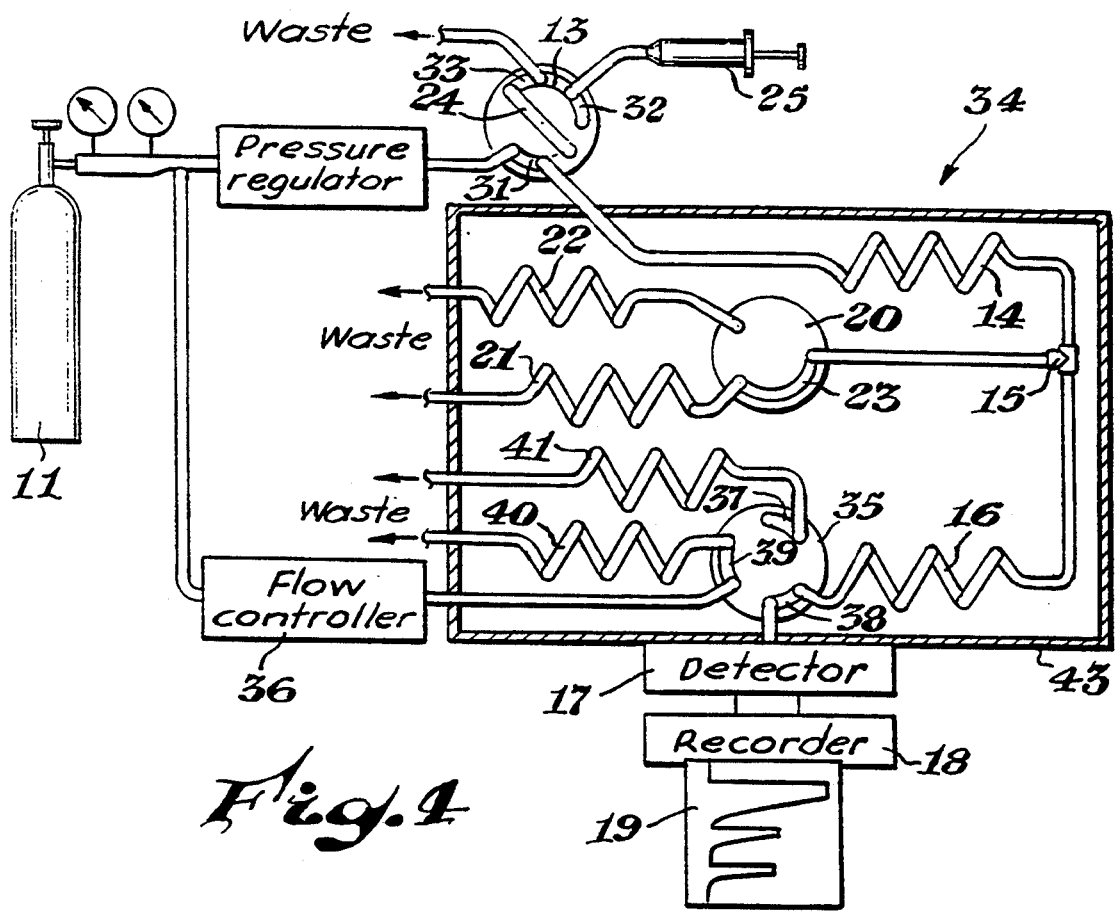
FIG. 4 is a part schematic and part full drawing of a vented capillary gas chromatograph of the instant invention that is similar to FIG. 1 except that a flow switching valve and a carrier gas flow controller are added.
Figure 5:
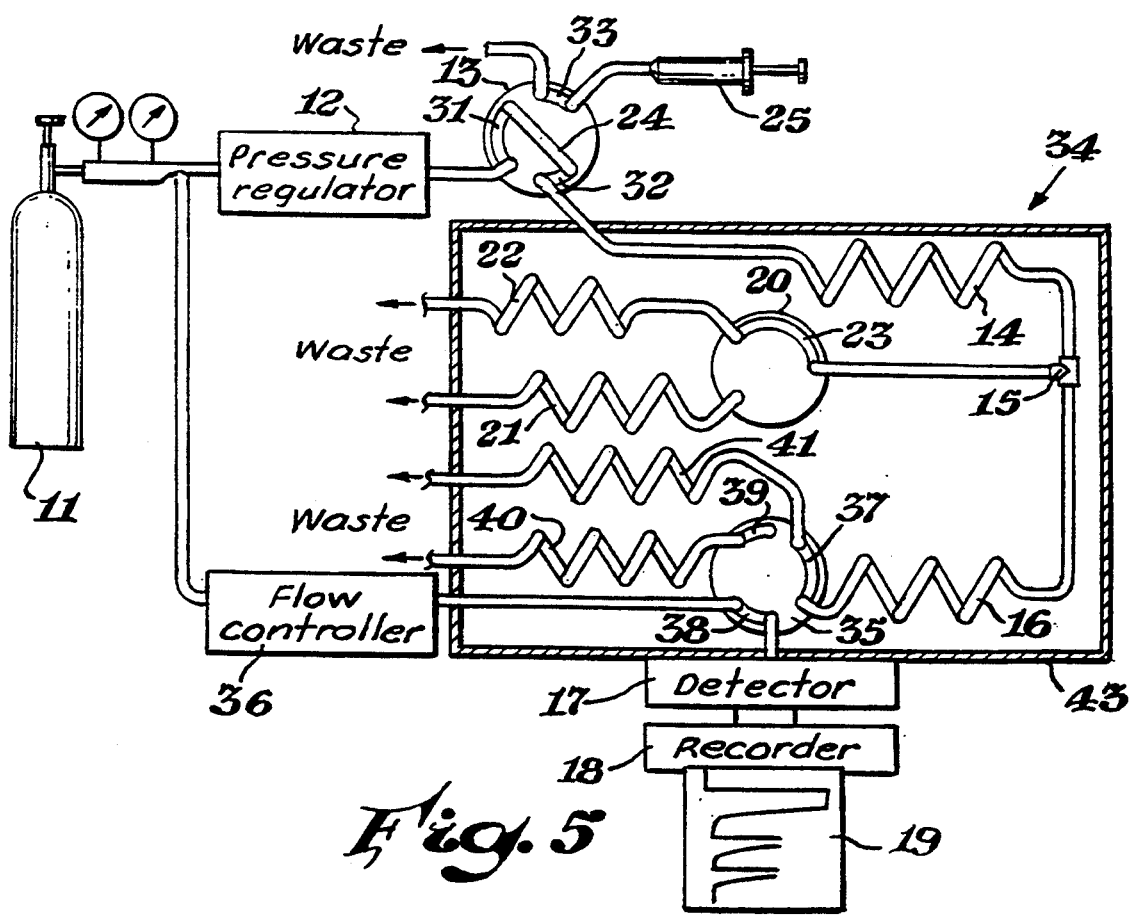
FIG. 5 shows the same apparatus as FIG. 4 but shows the injection valve in the inject position and shows the flow switching valve in the vent position wherein, during the venting step, carrier gas is flowed from the added carrier gas flow controller through the flow switching valve to the detector.

The instant invention, in another of its apparatus embodiments, is also an improvement on the type of vented capillary gas chromatograph shown in FIG. 1. Referring now to FIGS. 4 and 5, therein is shown a vented capillary gas chromatograph 34 in one embodiment of the instant invention. A comparison between FIG. 1 and FIGS. 4 and 5 will reveal many similarities. Therefore, the elements of FIGS. 4 and 5 that are the same as the elements of FIG. 1 will be given the same reference numerals. However, a comparison between FIG. 1 and FIGS. 4 and 5 will also reveal that a multi-position fluid flow switch having at least two positions, i.e., the flow switching valve 35, has been added to the system. In addition, a carrier gas flow controller 36 is connected by tubing to the cylinder 11 and to the switching valve 35 in order to supply gas to the switching valve 35. Also, the retention gap 14, the tee 15, the column 16, the divert valve 20, the bleed restrictor 21, the vent restrictor 22, the valve 37, the flow restrictor 40, and the column restrictor 41 are all contained in an oven 43.

As shown in FIG. 4, the switching valve 35 is in its first or analysis position. The switching valve 35 contains a first passageway 37, a second passageway 38 and a third passageway 39. When the switching valve 35 is in the position shown in FIG. 4, the outlet end of the column 16 is in fluid communication with the detector 17 via the passageway 38, and the tee 15 is in fluid communication with the bleed restrictor 21 via the passageway 23 in the divert valve 20. Preferably, when the switching valve 35 is in the position shown in FIG. 4, the carrier gas flow controller 36 is in fluid communication with the flow restrictor 40 via the passageway 39. In FIG. 4, the injection valve 13 is in its load position as discussed in the description of FIG. 2.

Referring now to FIG. 5, therein is shown the same apparatus as in FIG. 4 but with the switching valve 35 in a second or vent position, with the injection valve 13 in its inject position as discussed in the description of FIG. 3, and with the divert valve 20 in a position such that the tee 15 is in fluid communication with the vent restrictor 22 via the passageway 23. When the switching valve 35 is in the position shown in FIG. 5, the carrier gas flow controller 36 is in fluid communication with the detector 17 via the passageway 38, and the outlet end of the column 16 is in fluid communication with a column restrictor 41 via the passageway 37.

Like the flow controller 28 in FIGS. 2 and 3, it should be understood that the flow controller 36 in FIGS. 4 and 5 is but one of the many means for supplying a gas that could have been used. Also, like the switching valve 27 in FIGS. 2 and 3, it should be understood that the switching valve 35 in FIGS. 4 and 5 is but one of the many multi-position fluid flow switches that could have been used.

Further, it should be understood that the bleed restrictor 21, vent restrictor 22, flow restrictor 40, and column restrictor 41 all refer to any of a myriad of means for restricting flow such as capillary tubing, a pinched length of tubing, a packed bed, a flow control valve, a leaking fitting and a small orifice plate.

For purposes of the instant invention, "retention gaps" are column inlets with reduced retention power as compared to the separating part of an analytical column. Further explanation regarding the design and operation of retention gaps is described in Grob, On-Column Injection in Capillary Gas Chromatography, (1987) which is incorporated by reference for the purpose of illustrating typical prior art in the field of capillary gas chromatography.

The method of the instant invention will now be discussed with reference to FIGS. 2 and 3. In FIG. 2, a carrier gas, such as helium, is flowed from the cylinder 11, through the following elements: a pressure regulator 12; the injection valve 13, via a passageway 31 in the valve 13; the retention gap 14; the tee 15; the column 16; the switching valve 27, via the passageway 29; and, finally, to the detector 17. A small portion of this carrier gas flow flows from the tee 15, through the valve 27 via the passageway 42, and, finally, through the bleed restrictor 21.

A liquid sample, comprising a volatile solvent and at least one component of interest that is less volatile than the solvent, is contained by the syringe 25. The term "less volatile" means the atmospheric pressure boiling point of a component of interest is higher than that of the solvent such as at least twenty-five degrees centigrade higher or at least fifty degrees centigrade higher. With the liquid sample in the syringe 25, the plunger of the syringe 25 is depressed causing sample to flow through a passageway 32, through the injection loop 24 and then through a passageway 33 to waste.

This method is suitable for large volume on-column injection of sample. Using conventional capillary gas chromatography columns, the term "large volume" means an injection of more than about five microliters of sampler however, proportionately smaller volumes can be injected when smaller capillaries are used. When the injection valve 13 is actuated from its load position to its inject position, the passageways 31, 32, and 33 of the valve 13 are rotated from the position shown in FIG. 2 to the position shown in FIG. 3. At about the same time, the passageways 29, 30 and 42 of the valve 27 are also rotated from the position shown in FIG. 2 to the position shown in FIG. 3.

When the passageways 31, 32 and 33 of the valve 13 are actuated to the position shown in FIG. 3, then the liquid sample contained in the loop 24 is swept into the retention gap 14 by the flow of carrier gas. The sample undergoes a selective vaporization in the retention gap 14 into the carrier gas.

The term "selective vaporization" means when a sample is injected into the retention gap, then: (a) the carrier gas emerging from the retention gap initially contains a mole ratio of volatile solvent to less volatile components of interest that is greater than the mole ratio of volatile solvent to less volatile components of interest of the original sample, i.e., the carrier gas is "enriched" with the volatile solvent of the injected sample; but (b) the carrier gas emerging from the retention gap eventually contains a mole ratio of volatile solvent to less volatile components of interest which is less than than the mole ratio of volatile solvent to less volatile components of interest of the original sample, i.e., the carrier gas is "enriched" with the less volatile components of interest of the injected sample.

Referring still to FIG. 3, when the carrier gas emerging from the retention gap 14 is enriched with the volatile solvent of the injected sample, then at least a portion of the stream of carrier gas emerging from the retention gap 14 is flowed to waste via the connector 15, the passageway 30 in the flow switching valve 27 and the vent restrictor 22; the remaining portion is flowed into the column 16. The portion flowed to waste is more than one half of the stream of carrier gas flowing from the retention gap 14 enriched with solvent. Preferably, the portion flowed to waste is greater than ninety percent, and, more preferably, greater than ninety-nine percent of the stream of carrier gas flowing from the retention gap 14 enriched with solvent. During the venting operation described in the preceding sentence, carrier gas from the cylinder 11 is flowed via the flow controller 28 and the passageway 29 to the detector 17. However, it should be understood that although it is convenient to use the same gas in this step as is used as the carrier gas which is flowed through the retention gap 14, the same gas is not critical in the instant invention. Thus, a gas other than the carrier gas can be flowed to the detector 17 during this step.

Adjusting the internal diameter and length of the vent restrictor 22 is the primary means of adjusting the portion of carrier gas emerging from the retention gap 14 which flows through the vent restrictor to waste. Thus, the use of a larger internal diameter vent restrictor 22 will result in a larger portion of carrier gas emerging from the retention gap 14 which flows through the vent restrictor to waste and a smaller portion which flows into the column 16.

The carrier gas, or other gas, flowed to the detector 17 during the venting operation described above, is termed a "proxy" gas. The proxy gas is preferably flowed to the detector at a rate which is from about thirty percent to about four times the flow rate of the carrier gas through the retention gap 14. More preferably, the flow rate of the proxy gas is from one third to three times, yet even more preferably, from one half to two times, and, most preferably, approximately the same as the flow rate of the carrier gas through the retention gap 14. The purpose of the proxy gas is to continue feeding a gas to the detector 17 during the venting operation. When the detector 17 is a mass spectrometer or another detector operated under a vacuum, it is beneficial to continue feeding a gas to the detector 17 during the venting operation so the level of vacuum in the detector remains approximately constant. In this regard, it is preferable to adjust the flow controller 28 soy during the venting operation, the vacuum in the mass spectrometer is maintained at about the same level as during the step described in the next paragraph.

Referring now to FIG. 2, the final step of the method of the instant invention will be discussed in which the sample is flowed to the detector. When the stream of carrier gas emerging from the retention gap 14 is enriched with at least one component of interest of the injected sample, then the valve 27 is actuated to the position shown in FIG. 2 so at least a portion of the stream carrier gas emerging from the retention gap 14 is flowed through the chromatography column 16 and the passageway 29 to the detector 17.

Similar to adjusting the vent restrictor 22 during the venting operation, adjusting the internal diameter and length of the bleed restrictor 21 is the primary means of adjusting the portion of carrier gas emerging from the retention gap 14 which flows into the column 16 during the analysis operation. Thus, the use of a larger internal diameter bleed restrictor 21 will result in a larger portion of carrier gas emerging from the retention gap 14 which flows through the bleed restrictor 21 to waste and a smaller portion which flows into the column 16.

Preferably, the portion of the stream of carrier gas emerging from the retention gap 14 enriched with the volatile solvent of the injected sample which is vented to waste, and the portion of the stream of carrier gas emerging from the retention gap 14 enriched with a component of interest which is flowed through the capillary gas chromatography column 16 are such that at least about thirteen percent of each component of interest, relative to the amount of the component of interest in the original sample, is detected by the detector 17. Preferably, from eighty to ninety-five percent, more preferably, greater than ninety-five percent, and most preferably, one hundred percent of each component of interest, relative to the amount of the component of interest in the original sample, is detected by the detector 17.

EXAMPLE

An apparatus similar to that shown in FIGS. 2 and 3 is assembled. A Hewlett Packard model 5890 Series II gas chromatograph equipped with a model 5971A mass selective detector 17 is modified by adding a Valco C6W loop type sample injection valve 24 and a high temperature Valco 6-port C6UWT switching valve 27 mounted inside the column oven 43 of the gas chromatograph. The retention gap 14 is a fifteen meter length of 0.53 millimeter internal diameter deactivated fused silica tubing. The column 16 is a twenty meter length of 0.18 millimeter internal diameter fused silica tubing having a 0.4 micrometer thick stationary phase of DB-1, methyl silicone, from the J&W Scientific Company.

The connector 15 is a J&W Scientific Company 3-way union, catalog number 705-0731. A 0.3 meter length of 0.32 millimeter deactivated fused silica tubing is used between the connector 15 and the valve 27. The bleed restrictor 21 is a fifty centimeter length of 0.05 millimeter internal diameter fused silica tubing. The vent restrictor 22 is a sixty-five centimeter length of 0.32 millimeter internal diameter fused silica tubing. A 0.5 meter length of deactivated 0.32 millimeter internal diameter fused silica tubing is used to connect the detector 17 with the valve 27. The pressure regulator 12 is set to regulate the pressure of carrier gas, helium, at fifteen pounds per square inch gauge.

A 100 microliter internal volume loop 24 of TEFLON brand fluorocarbon polymer tubing is installed on the injection valve 13. The switching valve 27 is heated to 250 degrees centigrade. The flow controller 28 is set so the level of vacuum within the detector 17 is about the same when the valve 27 is in the position shown in FIG. 2 as when the valve 27 is in the position shown in FIG. 3.

The syringe 25 is filled with a sample containing at least one component of interest dissolved in methanol. The syringe 25 is used to load this sample into the loop 24. The flow switching valve 27 is switched to the position shown in FIG. 3 immediately before the injection valve 13 is switched to the position shown in FIG. 3. The valve 13 is switched back to the position shown in FIG. 2 twelve seconds later. The valve 27 is switched back to the position shown in FIG. 2 three and six tenths minutes later. The mass selective detector 17 is set to detect in the scan range of from 50 to 200 atomic mass units. The detector 17 detects a mass spectra of the components of interest.

What is claimed is:

1. In a vented capillary gas chromatograph suitable for on-column injection, the vented capillary gas chromatograph being especially suitable for use with a mass spectrometer detector, the vented capillary gas chromatograph comprising a means for supplying a carrier gas, a means for injecting a liquid sample, a retention gap, a connector, a capillary gas chromatography column, and a detector; the means for supplying a carrier gas, the means for injecting a liquid sample, the retention gap, the connector, the capillary gas chromatography column and the detector each being respectively in series fluid communication; a divert valve, the divert valve being in fluid communication with the connector; a vent restrictor, a bleed restrictor, the vent restrictor and the bleed restrictor each being in fluid communication with the divert valve so the divert valve can alternatively provide fluid communication between the connector and the vent restrictor or between the connector and the bleed restrictor; the column having an inlet end and an outlet end, the inlet end of the column being connected to the connector, wherein the improvement comprising: replacing the divert valve with a multi-position fluid flow switch having at least two positions, the flow switch being in fluid communication with a means for supplying a gas, with the connector, with the bleed restrictor, with the vent restrictor, with the outlet end of the column, and with the detector so when the flow switch is in a first position, the outlet end of the column is in fluid communication with the detector and the connector is in fluid communication with the bleed restrictor, and when the flow switch is in a second position, the means for supplying a gas is in fluid communication with the detector, the outlet end of the column is in fluid communication with the bleed restrictor and the connector is in fluid communication with the vent restrictor.

2. The apparatus of claim 1, wherein the multi-position fluid flow switch comprises at least one valve.

3. In a vented capillary gas chromatograph suitable for on-column injection, the vented capillary gas chromatograph being especially suitable for use with a mass spectrometer detector, the vented capillary gas chromatograph comprising a means for supplying a carrier gas, a means for injecting a liquid sample, a retention gap, a connector, a capillary gas chromatography column and a detector; the means for supplying a carrier gas, the means for injecting a liquid sample, the retention gap, the connector, the capillary gas chromatography column and the detector each being respectively in series fluid communication; a divert valve, the divert valve being in fluid communication with the connector; a vent restrictor, a bleed restrictor, the vent restrictor and the bleed restrictor each being in fluid communication with the divert valve so the divert valve can alternatively provide fluid communication between the connector and the vent restrictor or between the connector and the bleed restrictor; the column having an inlet end and an outlet end, the inlet end of the column being connected to the connector, wherein the improvement comprising:

a multi-position fluid flow switch having at least two positions, a flow restrictor and a column restrictor, the flow switch being in fluid communication with a source of gas, with the detector, with the outlet end of the column, with the column restrictor and with the flow restrictor so when the flow switch is in a first position, the outlet end of the column is in fluid communication with the detector, and when the flow switch is in a second position, the outlet end of the column is in fluid communication with the column restrictor while the detector is in fluid communication with the source of gas.

4. The apparatus of claim 3, wherein the multi-position fluid flow switch comprises at least one valve.

* * * * *

UNITED STATES PATENT AND TRADEMARK OFFICE
CERTIFICATE OF CORRECTION

PATENT NO. : 5,338,514
DATED : August 16, 1994
INVENTOR(S) : Paul L. Morabito, et al.

It is certified that error appears in the above-indentified patent and that said Letters Patent is hereby corrected as shown below:

On the title page, item [56] Reference Cited and Other Documents, insert the following references:

--5,001,071  1991  Morabito et al  436/161
  5,048,322  1991  Hiller et al    73/23.41
  4,962,042  1990  Morabito et al  436/161

Other Documents

K. Grob, "On-Column Injection in Capillary Gas Chromatography"; Huthig, N.Y. (1987), 357
Gordon M. Message, "Practical Aspects of Gas Chromatography/Mass Spectrometry":
John Wiley & Sons, pp 127-128 (1984)--

Signed and Sealed this

Thirtieth Day of January, 1996

Attest:

BRUCE LEHMAN

Attesting Officer

Commissioner of Patents and Trademarks